United States Patent
Pursiheimo et al.

(12) 
(10) Patent No.: US 6,287,416 B1
(45) Date of Patent: Sep. 11, 2001

(54) SAMPLING APPARATUS WITH REMOVABLE FILTER FOR CLEANING

(75) Inventors: Petri Pursiheimo; Claes Zetter, both of Turku (FI)

(73) Assignee: ABB Industry Oy, Helsinki (FI)

(*) Notice: Subject to any disclaimer, the term of this patent is extended or adjusted under 35 U.S.C. 154(b) by 0 days.

(21) Appl. No.: 09/319,461

(22) PCT Filed: Dec. 9, 1997

(86) PCT No.: PCT/FI97/00766
§ 371 Date: Jun. 7, 1999
§ 102(e) Date: Jun. 7, 1999

(87) PCT Pub. No.: WO98/26272
PCT Pub. Date: Jun. 18, 1998

(30) Foreign Application Priority Data

Dec. 10, 1996 (FI) ............................................ 964929

(51) Int. Cl.⁷ ....................................................... D21C 7/12
(52) U.S. Cl. ........................ 162/49; 162/198; 162/263; 162/251; 73/63; 73/863.85
(58) Field of Search .................. 73/63, 863.85; 162/49, 198, 251, 263

(56) References Cited

U.S. PATENT DOCUMENTS

| | | | |
|---|---|---|---|
| 3,688,563 | 9/1972 | Enarsson et al. | 73/63 |
| 4,683,207 * | 7/1987 | Waarvik | 435/311 |
| 4,880,973 * | 11/1989 | Reynolds | 250/253 |
| 6,062,073 * | 5/2000 | Patton et al. | 73/152.28 |

FOREIGN PATENT DOCUMENTS

| | | |
|---|---|---|
| 57663 | 5/1980 | (FI) . |
| 95839 | 12/1995 | (FI) . |

* cited by examiner

*Primary Examiner*—Dean T. Nguyen
(74) *Attorney, Agent, or Firm*—Kubovcik & Kubovcik

(57) ABSTRACT

The object of the invention is a sampling apparatus in a continuous industrial process for taking a sample (16) of the substance to be monitored (11). The sampling apparatus is located on the wall (11) of the pulp tank and it includes a sample chamber (14), which is equipped with a cover (13), and a filter (15). The sample chamber includes a closing device (18, 24), by means of which the connection from the pulp tank to the sample chamber can be closed, as a result of which the filter remains in the sample chamber in the space between the cover and the closing device. The filter can be pulled out of the sample chamber for cleaning after the cover of the sample chamber has been opened. Another object of the invention is a sampling method and a cleaning method for the sampling apparatus presented.

7 Claims, 4 Drawing Sheets

SAMPLING APPARATUS WITH REMOVABLE FILTER FOR CLEANING

BACKGROUND OF THE INVENTION

The object of the invention is a sampling apparatus in a continuous industrial process for taking a sample of the substance to be monitored, such as a pulp or fluid, the sampling apparatus being placed adjacent to the substance to be monitored, such as on the wall of the pulp tank or liquid tube, and the sampling apparatus including a sample chamber equipped with a cover and a filter for taking the sample from the substance to be monitored through the filter to the sample chamber.

In continuous industrial processes, for example, in the paper industry in processing paper pulp, it is necessary in order to control the process to take samples at different stages of the process. Different sampling apparatuses and sampling methods have been developed for this purpose. The simplest way of taking a sample in a continuous process is to install a tap, for example, in the pulp tank or a tube connected to it When a sample is needed the tap is turned on. After the sample has been taken the tap is turned off.

However, the known sampling apparatuses have disadvantages. For example, a sample cannot be taken of a thick pulp using a tap, because the pulp dogs the tap. Neither do filters located in conjunction with the tap eliminate these problems, because then the filters easily get clogged.

SUMMARY OF THE INVENTION

The purpose of the invention is to eliminate the above-mentioned problem and provide a new sampling apparatus which does not have the above-mentioned disadvantages. It is characteristic of the sampling apparatus relating to the invention that the sample chamber of the sampling apparatus incorporates a dosing device, by means of which the connection to the sample chamber from the tank or the like containing the substance to be monitored can be closed, leaving the filter in the sample chamber in a space between the cover and the closing device. Because the filter of the sampling apparatus is cross-directionally smaller than the opening of the sample chamber cover, the filter can be pulled out of the sample chamber after opening the cover of the sample chamber.

According to one advantageous embodiment of the invention, the body of the sampling apparatus's sample chamber is mainly cylindrical, and the cylindrical filter can be fitted concentrically inside the cylindrical body.

According to another advantageous embodiment, the closing device of the sampling apparatus is an interior cover, which is situated at the end of the cylindrical body that is in the tank or the like containing the substance to be monitored, and the interior cover can be moved in the direction of the axis of the body's cylinder and pushed against the end of the body to close the sample chamber. In such a case, the interior cover is closed by pulling it against the end of the body by means of actuator cylinders, which are situated between the body and the interior cover.

The actuators can be, for example, pneumatic or hydraulic cylinders. The most advantageous number of actuator cylinders placed at regular intervals on the circumference of the body cylinder is three. The linear motion of the interior cover has been further ensured using three guide bars, which have been placed on the circumference between the actuator cylinders.

According to a third advantageous embodiment, the cylindrical filter is fastened to the interior cover with a screw or the like in such a way that the filter can be unfastened and removed for cleaning.

According to a fourth advantageous embodiment of the invention the closing device of the sampling apparatus incorporates a fixed interior cover or a similar part, which is situated near the end of the cylindrical body that is in the tank or the like containing the substance to be monitored. The closing device has a cylindrical slide, which is moved, for example, by means of a pressure medium and which moves in the direction of the cylindrical body's axis and presses against the fixed interior cover when closing the device.

Another object of the invention is a sampling method in a continuous industrial process which does not have the disadvantages of the known methods. According to the method, to take a sample of the substance to be monitored, such as a pulp or fluid, the sampling apparatus is placed adjacent to the substance to be monitored, such as on the wall of the pulp tank or liquid tube, and a fluid sample of the substance to be monitored is taken through a filter into the sample chamber.

It is characteristic of the method relating to the invention that the sample chamber of the sampling apparatus is at least partly located inside the tank or the like containing the substance to be monitored, in which case the pressure in the tank presses a fluid sample of the substance to be monitored through the filter into the sample chamber of the sampling apparatus.

According to one advantageous embodiment of the sampling method, the sampling method is continuous in such a way that fluid samples of the substance to be monitored are continuously obtained without disturbing the process taking place in the tank.

In the method, that the substance to be monitored, such as, for example, paper pulp, is taken into the sampling apparatus located in conjunction with the tank or the like containing the substance to be monitored, and the pressure in the tank presses the pulp to be monitored against the filter of the sampling apparatus. No suction is used in the method, but instead, normal pressure conditions in the process are utilised. A pressure difference is not produced separately, as there already exists a pressure difference in the process due to the overpressure prevailing in the tank. The filter prevents the passage of solid particles of a predetermined size, but the liquid phase and the colloidal sample phase of the pulp to be monitored are passed through the filter into the sample chamber. From their the sample to be analysed is passed on further for examination.

A further objective of the invention is a method for cleaning the sampling apparatus in a continuous industrial process in which samples are continuously taken from the substance to be monitored, such as a pulp or fluid, and in which a sampling apparatus equipped with a cover is placed adjacent to the substance to be monitored, such as on the wall of the pulp tank or liquid tube in such a way that the fluid sample is taken from the substance to be monitored through the filter into the sample chamber of the sampling apparatus.

The filter of the sampling apparatus is usually the most problematic part of the apparatus because the pulp in the tank tends to dog the filter. In the known apparatuses, it is usually not possible to remove the filter while the process is under way, so there are different methods for cleaning the filter. A generally known method is to arrange a system for blowing air through the filter from the sample chamber towards the pulp tank. In such a case the pulp fibres caught in the filter are released from the surface of the filter and they return to the pulp.

At some stage, however, the filter usually gets so badly clogged, that no air blowing or rinsing procedures can open the pores of the filter. In such a case, the filter needs to be cleaned more thoroughly. This is usually not possible before the process is discontinued and the pulp tank emptied.

The purpose of this invention is to create a method through which the filter of the sampling apparatus can be deaned without stopping the process. It is characterisic of the cleaning method relating to the invention that the cleaning of the sampling apparatus's filter comprises the following steps, the closing device, which is situated at that end where the tank or the like containing the substance to be monitored is, is closed, in which case the process in the tank is not disturbed, but the filter remains in the sample chamber in the space between the cover and the closing device, the sample chamber is emptied, the cover opened and the filter pulled out for cleaning, the filter is pushed back to its place, the cover closed and the closing device opened, after which the sampling apparatus is again available for continuous use.

According to one advantageous embodiment of the invention the cleaning of the filter comprises the following steps, the closing device of the sampling apparatus is closed by pushing the interior cover that can be moved in the direction of the axis of the cylindrical body against the end of the body, the sample chamber is emptied, the cover opened and the filter detached from the interior cover, the filter is pulled out for cleaning.

According to another advantageous embodiment of the invention the cleaning of the filter comprises the following steps, the closing device of the sampling apparatus is closed by pushing the cylindrical slide situated inside the body and moving in the direction of its axis against the fixed interior cover, the cover of the sample chamber is opened, in which case the filter supported between the cover and the fixed interior cover is released and can be removed for cleaning.

BRIEF DESCRIPTION OF THE DRAWINGS

In the following, the invention is described using examples with reference to the accompanying drawings, in which.

DETAILED DESCRIPTION OF THE PREFERRED EMBODIMENT

Figure 1:
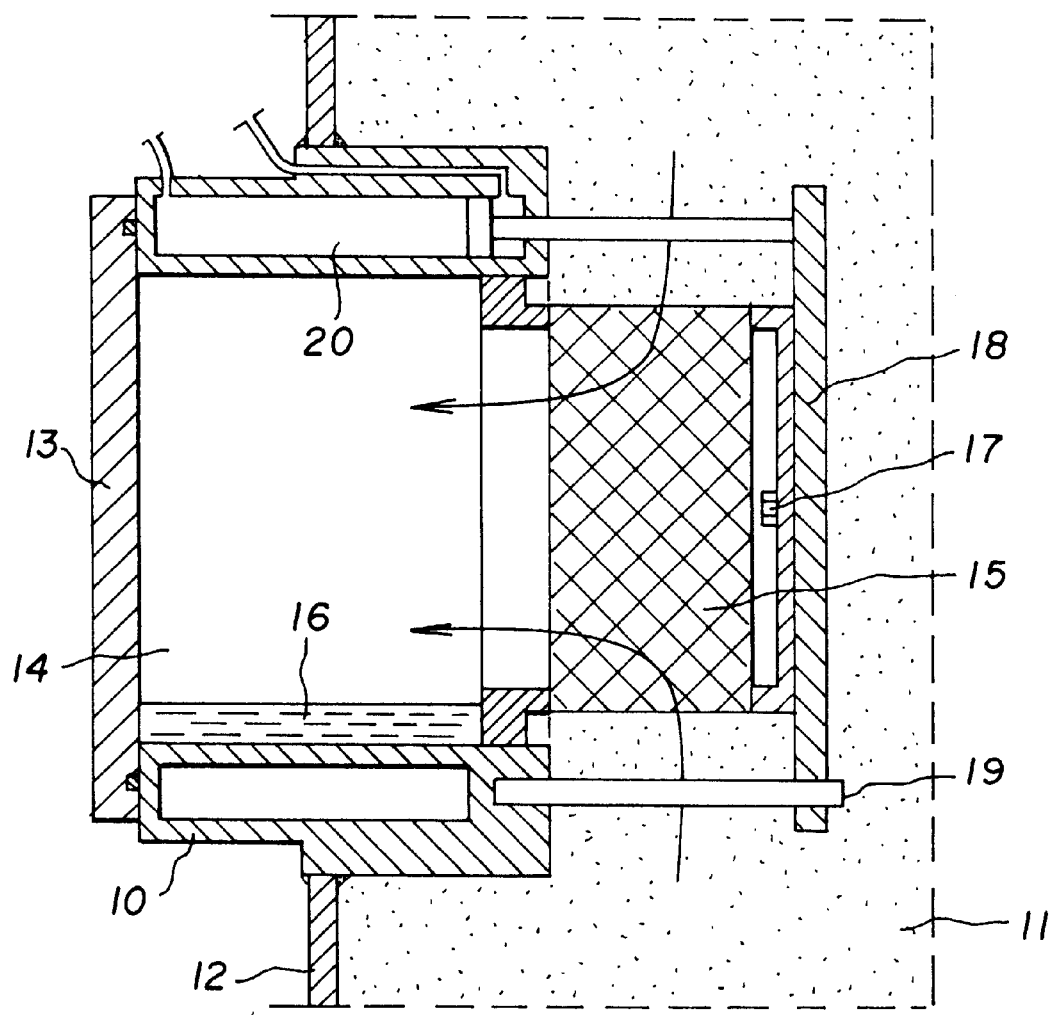
FIG. 1 shows a sectional view of the sampling apparatus relating to the invention with the closing device open, seen from the side.

FIG. 1 snows one embodiment of the sampling apparatus relating to the invention. The body of the sampling apparatus is a cylinder 10, which has been fitted in the opening of the wall 12 of the tank containing pulp to be sampled 11. The cylinder 10 has been closed with a cover 13 from outside the tank in such a way that a sample chamber 14 is formed inside the cylinder 10. The fluid sample that is separated from the pulp 11 is taken through the cylindrical filter 15 into the sample chamber 14. In FIG. 1, the fluid 16 forming the sample is at the bottom of the cylinder.

From the pulp 11 in the tank, new fluid is continuously filtered through the filter 15 into the sample chamber 14 due to the overpressure prevailing in the tank. Therefore, samples can continuously be taken for analysis from the sample chamber 14, although the process involving the pulp 11 in the tank is in progress. Thus a continuous-working sampling apparatus that does not disturb the process is created. FIG. 1 does not show the piping relating to the sampling method through which the sample is fed on into the analysing apparatus.

The filter 15 of the sampling apparatus is cleaned by first closing the closing device, which closes the connection between the tank and the sample chamber 14. In the example of one embodiment shown in FIG. 1, the closing device is the interior cover 18, which closes the sample chamber 14 from inside the tank. With the actuator cylinders 20, the interior cover 18, guided by the bars 19, is pulled against the cylinder 10. The actuator cylinders 20 function by means of a pressure medium, which can be a liquid or a gas. In such a case, a closed space is formed in the sample chamber 14 between the cover 13 and the interior cover 18. The filter 15 is attached to the interior cover 18 with a screw 17 in such a way that when the cover 18 is moved, the filter 15 moves with it, following the inner surface of the cylinder 10. The closed position of the closing device is shown in FIG. 2.

Figure 2:
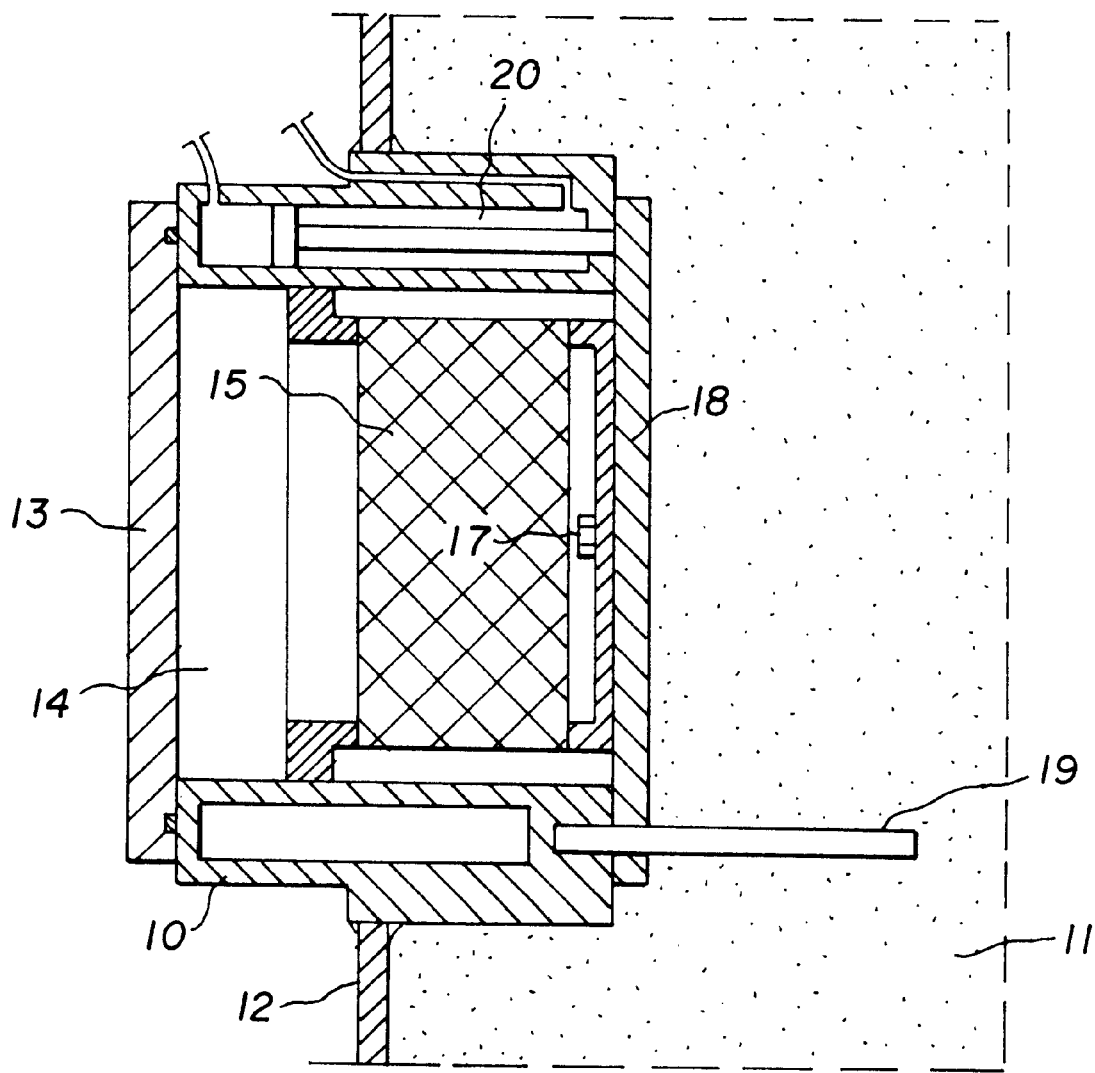
FIG. 2 corresponds to FIG. 1 and shows the sampling apparatus with the closing device closed.

FIG. 2 shows the sampling apparatus in FIG. 1 with the closing device closed. In such a case, the sample chamber 14 is closed with an interior cover 18 on the inside of the tank. After that the sample chamber 14 is emptied and the cover 13 located outside the tank is opened. The screw 17 attaching the filter 15 to the interior cover 18 is undone and the filter is pulled out for cleaning. After cleaning, the above-mentioned procedure is performed in reverse order. After the interior cover 18 has been reopened, the sampling apparatus is again ready for taking samples. The removal and cleaning of the filter do not in any way disturb the process which is going on in the tank.

Figure 3:
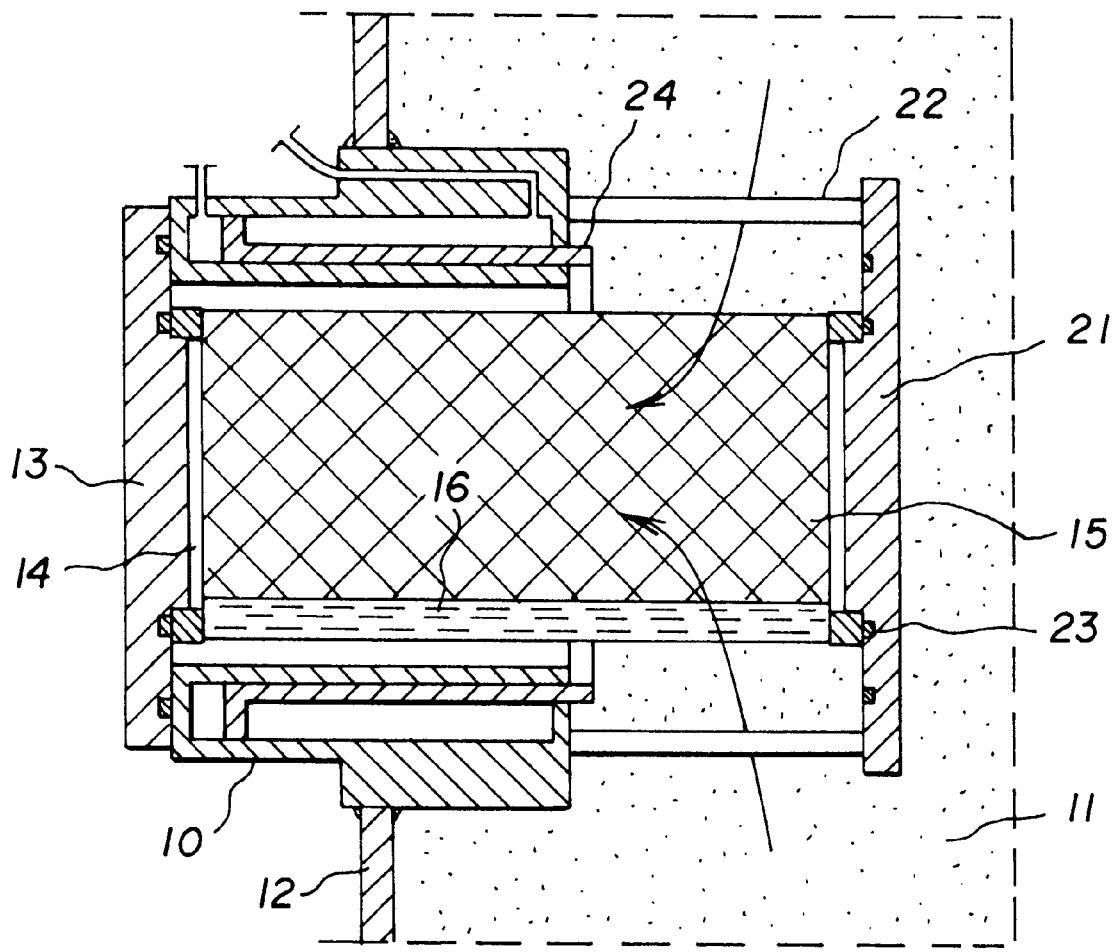
FIG. 3 corresponds to FIG. 1 and shows another embodiment of the sampling apparatus.

FIG. 3 shows another embodiment of the sampling apparatus. In it, the body of the sampling apparatus is also a cylinder 10, which has been fitted into the opening of the wall 12 of the tank containing the sample pulp 11, and the cylinder 10 has been closed from outside the tank with a cover 13. Inside the tank, a fixed cover 21 has been attached to the cylinder 10 by means of bars 22. The filter 15 has been pressed between the fixed cover 21 inside the tank and the cover 13 closing from the outside. The sealings 23 at both ends of the filter 15 seal the ends in such a way that the sample chamber 14 is formed completely inside the filter 15. The fluid sample is passed through the cylindrical filter 15 to the sample chamber 14. In FIG. 3, the sample fluid 16 that is separated from the pulp 11 is at the bottom of the filter 15.

When the filter 15 of the sampling apparatus in FIG. 3 needs to be cleaned more thoroughly, in this solution, too, the connection from the pulp 11 inside the tank to the sample chamber 14 must be closed. This is done by means of a special cylindrical slide 24, which can be moved by means of a pressure medium. The cylindrical slide 24 is pushed against the fixed interior cover 21, and the sample chamber 14 is closed. The closed position of the closing device is shown in FIG. 4.

Figure 4:
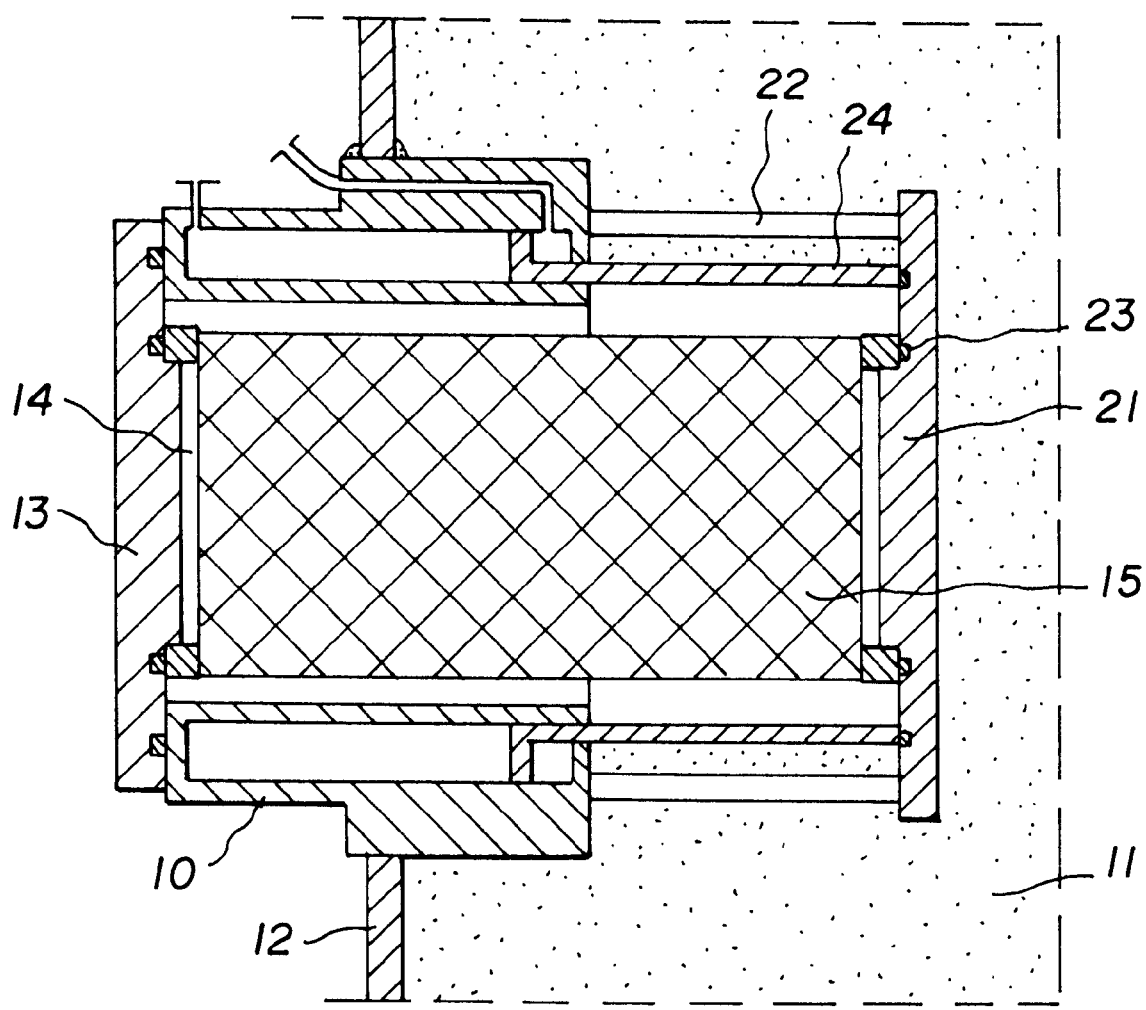
FIG. 4 corresponds to FIG. 3 and shows the sampling apparatus with the closing device closed.

FIG. 4 shows the sampling apparatus in FIG. 3 with the closing device closed. The cylindrical slide 24 is pushed against the fixed interior cover 21, after which the connection from inside the tank to the sample chamber 14 is closed. After that, the sample chamber 14 is emptied and the cover 13 opened. The filter 15 is pulled out and cleaned. After cleaning, the above-mentioned procedure is performed in reverse order. After the cylindrical slide 24 has been pulled away, the sampling apparatus is again ready for taking samples. In this embodiment, too, the removal and cleaning of the filter did not disturb the process which was going on in the tank.

It is obvious to a person skilled in the art that the different embodiments of the invention may vary within the scope of the claims presented below.

What is claimed is:

1. A sampling apparatus for taking a sample of a substance to be monitored from a receptacle containing the substance to be monitored, said apparatus comprising:
   A) a sample chamber located in a wall of said receptacle and extending into said receptacle, said sample chamber having a first opening outside of the receptacle and a second opening inside of the receptacle;
   B) a cover detachably secured to said sample chamber and closing said first opening;
   C) a opening and closing means provided adjacent said second opening of the sample chamber for opening and closing said second opening, and
   D) a tubular filter removably positioned in the sample chamber and separating an interior of the chamber from the sample to be monitored,
   wherein when said opening and closing means is opened, said sample to be monitored flows through said filter into said sample chamber.

2. A sampling apparatus as recited in claim 1, wherein the tubular filter is cross-directionally smaller than the first opening of said sample chamber such that the filter can be removed from the sample chamber after the cover has been detached.

3. A sampling apparatus as recited in claim 1, wherein the sample chamber is cylindrical and the tubular filter is fitted concentrically inside the sample chamber.

4. A sampling apparatus as recited in claim 1, wherein the opening and closing means comprises an interior cover which closes said second opening and is movable in the direction of the axis of the sample chamber for opening the second opening.

5. A sampling apparatus as recited in claim 4, wherein the opening and closing means further comprises two or more actuator cylinders connected to said interior cover and movable in the direction of the axis of the cylindrical sample chamber for pushing the interior cover away from and opening said second opening or pulling the interior cover against and closing said second opening.

6. A sampling apparatus as recited in claim 5, wherein the tubular filter is detachably fastened to said interior cover.

7. A sampling apparatus as recited in claim 1, wherein the the opening and closing means comprises:
   A) a fixed cover means spaced apart from said second opening, and
   B) a cylindrical slide which is movable in the direction of the axis of the cylindrical body and can be pushed against the fixed cover means to close the second opening.

* * * * *